United States Patent
Ben-David et al.

(10) Patent No.: US 9,453,285 B2
(45) Date of Patent: Sep. 27, 2016

(54) PROCESSES FOR PREPARING N-ETHYL-2-METHYLPYRIDINIUM BROMIDE AND N-ETHYL-3-METHYLPYRIDINIUM BROMIDE

(71) Applicant: BROMINE COMPOUNDS LTD., Be'er Sheva (IL)

(72) Inventors: Iris Ben-David, Ashdod (IL); Gershon Miaskovski, Be'er Sheva (IL); Igor Kompaniets, Be'er Sheva (IL)

(73) Assignee: BROMINE COMPOUNDS LTD., Be'er-Sheva (IL)

( * ) Notice: Subject to any disclaimer, the term of this patent is extended or adjusted under 35 U.S.C. 154(b) by 156 days.

(21) Appl. No.: 14/220,631

(22) Filed: Mar. 20, 2014

(65) Prior Publication Data

US 2014/0262818 A1 Sep. 18, 2014

Related U.S. Application Data

(63) Continuation-in-part of application No. PCT/IL2012/000348, filed on Sep. 23, 2012.

(60) Provisional application No. 61/803,828, filed on Mar. 21, 2013, provisional application No. 61/537,622, filed on Sep. 22, 2011.

(51) Int. Cl.
*C07D 213/20* (2006.01)
*C25B 1/24* (2006.01)
*C25B 1/02* (2006.01)

(52) U.S. Cl.
CPC ............... *C25B 1/24* (2013.01); *C07D 213/20* (2013.01); *C25B 1/02* (2013.01)

(58) Field of Classification Search
CPC .................................................. C07D 213/20
See application file for complete search history.

(56) References Cited

U.S. PATENT DOCUMENTS 6,118,000 A 9/2000 Frenier

FOREIGN PATENT DOCUMENTS

| JP | 10-316661 | 12/1998 |
| JP | 2000-226360 | 8/2000 |
| JP | 3821977 | 8/2000 |
| JP | 3821977 B2 * | 9/2006 |

OTHER PUBLICATIONS

Extended European Search Report issued in European Application No. 12 83 3862.1 dated Mar. 16, 2015.
Baldwin et al., "A Biomimetic Approach to the Manzamine Alkaloids; Model Studies," *Tetrahedron Letters*, 1994, pp. 7829-7832, vol. 35, No. 42.
Provencher et al., "Pyridinium-based protic ionic liquids as electrolytes for $RuO_2$ electrochemical capacitors," *Journal of Power Sources*, 2010, pp. 5114-5121, vol. 195.
Murrill, "Halides and Perhalides of the Picolines", Journal of the American Chemical Society, 21, Dec. 31, 1899, pp. 828-854.
Ploquin et al., Journal of Heterocyclic Chemistry, vol. 17, 1980, pp. 997-1008.
International Search Report for PCT/IL2012/000348 mailed Dec. 6, 2012.
Chinese Office Action issued in Application No. 201280057461.1 dated Feb. 6, 2015 (w/ trans).

* cited by examiner

*Primary Examiner* — Nicholas A Smith
(74) *Attorney, Agent, or Firm* — Nixon & Vanderhye P.C.

(57) ABSTRACT

A process for preparing an aqueous solution of N-ethyl-2-methylpyridinium bromide (2-MEPy), comprising reacting 2-picoline and ethyl bromide in a pressure reactor at a temperature above the melting point of the reaction mixture, combining the reaction product with water, wherein said reaction product consists essentially of 2-MEPy in a liquid form, and recovering an aqueous solution of 2-MEPy.

4 Claims, No Drawings

PROCESSES FOR PREPARING N-ETHYL-2-METHYLPYRIDINIUM BROMIDE AND N-ETHYL-3-METHYLPYRIDINIUM BROMIDE

CROSS-REFERENCE TO RELATED APPLICATION(S)

This application is a continuation-in-part (CIP) of International Application No. PCT/IL2012/000348 filed on Sep. 23, 2012, which claims the benefit of U.S. Provisional Patent Application No. 61/537,622, filed on Sep. 22, 2011, the entire contents of each of which is incorporated herein by reference. This application also claims the benefit of U.S. Provisional Patent Application No. 61/803,828, filed on Mar. 21, 2013, the entire contents of which are incorporated herein by reference.

FIELD OF THE INVENTION

The present invention relates to environmentally-friendly processes for preparing the compounds N-ethyl-2-methylpyridinium bromide and N-ethyl-3-methylpyridinium bromide, allowing the recovery of said compounds in the form of highly concentrated aqueous solutions.

BACKGROUND OF THE INVENTION

Experimental work carried out in our laboratories shows that N-ethyl-2-methylpyridinium bromide and N-ethyl-3-methylpyridinium bromide (abbreviated herein 2-MEPy and 3-MEPy, respectively) are useful as additives in the electrolyte of hydrogen/bromine electrochemical cells. The electrolyte is an aqueous solution of hydrogen bromide. The operation of hydrogen/bromine electrochemical cells is based on the electrolysis of hydrogen bromide, and the conversion of the electrolysis products, i.e., hydrogen and elemental bromine, back to hydrogen bromide. During charge, an electric current supplied from an external source drives the electrolysis of hydrogen bromide, generating hydrogen ($H_2$) and elemental bromine ($Br_2$), which are stored separately in suitable tanks located externally to the cell. $H_2$ and $Br_2$ are fed back to the cell during discharge and are reacted to give hydrogen bromide, thereby producing electric energy. There is a need to keep the elemental bromine in a form which can be readily stored and pumped over a broad temperature range, such that it can be used without interfering with the operation of the cell. Notably, 2-MEPy and 3-MEPy form stable liquid complexes with elemental bromine in aqueous hydrogen bromide solutions; the complexes do not undergo solidification over a broad temperature range, throughout the entire operation period of the cell, despite the variation of the electrolyte concentration (at the beginning of the charge state, the concentration of hydrogen bromide may be as high as 30-50 wt %).

In their most general form, the synthetic routes for preparing 2-MEPy are based on the reaction between 2-picoline and ethyl bromide (abbreviated Et-Br), as shown by the following scheme:

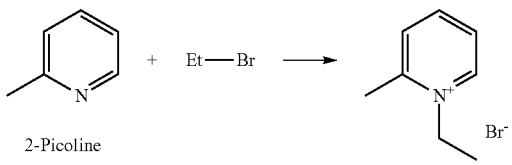

Murrill [Journal of the American Chemical Society, 21, p. 828-854 (1899)] described a reaction in which the reactants were heated together under a reflux condenser. The author reported that at the end of the reaction, which lasted three or four hours, the reaction mass was allowed to solidify and the product was crystallized from ethanol to give transparent, colorless, hygroscopic crystals.

The reaction depicted above was also carried out in acetonitrile as a solvent, as reported by Ploquin et al. [Journal of Heterocyclic Chemistry, 17, p. 997-1008 (1980)].

In view of the utility of 2-MEPy as an additive in the electrolyte of hydrogen/bromine cells, it may be advantageous to provide the compound directly in the form of a concentrated aqueous solution, which can be readily injected into, and mixed with, the aqueous hydrogen bromide electrolyte used in the cell. It has now been found that the reaction between 2-picoline and ethyl bromide can be carried out either in a dry medium (solvent-free reaction mixture) or in water as a solvent, to give the 2-MEPy product in a good yield and purity levels acceptable for the application of 2-MEPy in hydrogen/bromine electrochemical flow cells. Thus, the present invention provides processes capable of affording the aqueous concentrate of 2-MEPy in a direct manner, which processes are devoid of the formation, isolation and purification of the compound in a solid state.

One aspect of the invention relates to a process for preparing an aqueous solution of N-ethyl-2-methylpyridinium bromide (2-MEPy), comprising reacting 2-picoline and ethyl bromide in a pressure reactor at a temperature above the melting point of the reaction mixture, combining the reaction product with water, wherein said reaction product consists essentially of 2-MEPy in a liquid form, and recovering an aqueous solution of 2-MEPy.

The reaction is free of solvent. Most preferably, the process does not involve the preparation or isolation of 2-MEPy in a solid form. Thus, according to the present invention, the solvent-free reaction mixture is heated to a temperature of preferably not less than 90° C., and more preferably not less than 95° C., such that the progressively formed 2-MEPy is maintained in a liquid form, providing an easily stirred reaction mass. The reaction-derived molten 2-MEPy is combined directly with water to form a clear aqueous solution.

The reactants may be used in equimolar amounts. However, it is generally preferred to carry out the reaction with one of the reactants being used in excess. The excess of ethyl bromide or the picoline may be up to 50% (molar), providing an easily stirrable reaction mixture. However, usually a lower excess of ethyl bromide or the picoline (e.g., in the range from 1 to 15 molar %) is sufficient for running the reaction conveniently.

According to one embodiment of the invention, the process comprises introducing the entire amounts of the reactants into the pressure reactor and then starting and advancing the reaction by slowly heating the reaction mixture in the sealed reactor to about 100° C. However, it is generally more preferred to gradually feed one of the reactants (or both) into the reactor over a period of time of not less than one hour under heating, following which the reactor is maintained for an additional period of time at a temperature that is sufficiently high for preventing solidification of the reaction mass (a "cooking period").

Thus, according to one embodiment of the invention, the process comprises charging a pressure reactor with 2-picoline, sealing and heating the reactor, gradually feeding ethyl bromide, preferably in an excess of about 1 to 10 molar %, allowing the reaction to reach completion at a temperature above 95° C., to form a reaction mass consisting essentially of 2-MEPy in a liquid form, and combining the liquid reaction mass with water.

The pressure reactor, which contains 2-picoline, is sealed and heated, preferably to a temperature above 70° C., e.g., from 80 to 110° C., following which the gradual addition of the ethyl bromide is started and allowed to continue, preferably in a continuous manner, for not less than 60 minutes. On a commercial scale, the addition period of ethyl bromide may last at least 180 minutes. Upon completion of the addition of ethyl bromide, the reaction is maintained under heating at a temperature above 95° C., e.g., from 95 to 110° C., for not less that 30 minutes whereby the reaction is completed, as indicated by the stabilization of the pressure in the reactor. Under the conditions set forth above, the reaction mixture, which during the gradual addition of the ethyl bromide consists of two distinct phases, progressively transforms into homogeneous reaction mass consisting essentially of 2-MEPy in a liquid form, with no solidification of the product taking place.

The reaction can be carried out under inert atmosphere to prevent side reactions. Such an atmosphere can be provided by inert gases such as nitrogen, argon and the like. Although the chemical reaction may start under atmospheric pressure, it is possible, following the introduction of the 2-picoline starting material, to pump the inert gas from the reactor, such that the addition of ethyl bromide would start under sub-atompsheric pressure.

Upon completion of the synthesis stage, the reaction mixture consists essentially of 2-MEPy in a liquid form, i.e., at least 70% by weight, and preferably at least 85% by weight of the reaction mass consists of the desired product. Any residual amount of a starting material employed in excess is removed from the reaction vessel by means of methods known in the art, e.g., evaporation of ethyl bromide, removal under vacuum or addition of water followed by azeotroic distillation. The latter option can be applied when either 2-picoline or ethyl bromide is used in excess, in which case the amount of water added is adjusted to serve two useful purpose: the azeotropic distillation and the formation of a solution of the product.

The liquid 2-MEPy reaction product is combined with water, to form the contemplated aqueous solution. To this end, de-ionized water is used, such that the concentration of the 2-MEPy solution is adjusted within the range from 40 to 92% by weight, and preferably between 65 to 90%. The product is collected in the form of an aqueous solution, which can be directly applied as an additive for the HBr electrolyte solution in accordance with the present invention.

Another aspect of the invention relates to a process for preparing an aqueous solution of 2-MEPy, comprising reacting 2-picoline with ethyl bromide in aqueous medium. It should be noted that water is normally not a solvent of choice in a reaction between amine and alkyl halide, in view of the hydrolysis of the alkyl halide in an aqueous basic environment, eventually leading to the formation of an amine hydrohalide by-product. In the present case, it has been found that 2-picoline hydrobromide is indeed formed when the reaction takes place in water; the larger the amount of water present in the reaction mixture, the higher is the level of the by-product. However, it has been found that the presence of 2-picoline hydrobromide in an aqueous solution of the 2-MEPy product does not interfere with the contemplated application of the aqueous concentrate in hydrogen/bromine electrochemical flow cells. Stated otherwise, the use of water as a solvent in the reaction between 2-picoline and ethyl bromide allows the direct formation of an aqueous concentrate of 2-MEPy, which, despite the presence of 2-picoline hydrobromide therein, is still perfectly acceptable for use as additive in hydrogen/bromine electrochemical flow cells.

The reaction in the aqueous medium is carried out by charging a pressure reactor with the reactants and water. The amount of water needed for maintaining a stirrable reaction mixture is generally about 5 to 20 weight % relative to the total weight of the reaction mixture. For example, 2-picoline and water are introduced into the reactor in a weight ratio of 10:1 to 2:1. The reactor is then sealed and heated to a temperature in the range from 80° C., e.g., from 80 to 100° C. At this point the gradual addition of ethyl bromide is started and continued for not less than 60 minutes at a temperature in the range from 80 to 115° C. Having completed the addition of ethyl bromide, a cooking period is applied, during which the reactor is maintained at a temperature of about from 95 to 115° C. for not less than 60 minutes, following which the residual amount of the reactant employed in excess is removed by azeotropic distillation and water may be added to give the aqueous concentrate which typically contains, in addition to 70-85 wt % 2-MEPy, also from 3 to 7 wt % 2-picoline hydrobromide.

The experimental results reported below indicate that the compound N-ethyl-3-methylpyridinium bromide (abbreviated 3-MEPy) is also useful as an additive in hydrogen/bromine cells. Furthermore, mixtures of 2-MEPy and 3-MEPy can also be used in such cells. A process for preparing an aqueous solution of 3-MEPy, comprising reacting 3-picoline with ethyl bromide in aqueous medium therefore forms another aspect of the invention. The conditions of the preparation of 3-MEPy are identical to those set forth above for 2-MEPy.

It is also possible to react a mixture consisting of 2-picoline and 3-picoline with ethyl bromide in a pressure reactor under the conditions described above, i.e., charging a pressure reactor with a mixture of 2-picoline and 3-picoline (e.g., in a molar ratio ranging from 5:1 to 1:5), heating the reaction mixture to a temperature of preferably not less than 90° C., gradually feeding ethylbromide to the reactor, further heating the solvent-free reaction mixture, either during or on completion of ethylbromide addition (e.g., to a temperature between 100 and 130° C.), such that the progressively formed mixture of 2-MEPy and 3-MEPy is maintained in a liquid form, providing an easily stirred reaction mass. At the end of the reaction, the pressure is released and the reaction-derived molten mixture consisting of 2-MEPy and 3-MEPy is combined with water to form a clear aqueous solution, with product concentration which is preferably not less than 70 weight %.

The concentrated aqueous solutions formed by the processes described above form another aspect of the invention. Thus, the invention relates also to a concentrated aqueous solution of 2-MEPy, 3-MEPy or a mixture thereof, with the concentration of the solution being from 40 wt % to 92 wt %, more preferably from 65 wt % to 90 wt %. The aqueous solutions provided by the present invention are clear and characterized in that they contain 2-MEPy (or 3-MEPy) which was "isolated in a non-solid form". By the term "isolated in a non-solid form" is meant that the 2-MEPy (or 3-MEPy) was not prepared in a solid (e.g., crystalline) form, and was not converted nor stored in a solid form. The aqueous solution of the invention may contain 2-MEPy or 3-MEPy in an individual form or in the form of mixtures, e.g., binary mixtures in which the molar ratio between the 2-MEPy and 3-MEPy is preferably from 1:5 to 5:1, more preferably from 1:4 to 4:1, e.g., from 1:3 to 3:1.

EXAMPLES

Example 1

Preparation of 2-MEPy Using a Large Excess of Ethyl Bromide

A pressure reactor was equipped with a mechanical stirrer with a magnetic relay and a thermocouple well. The reactor was purged with nitrogen and then charged with 2-picoline (95 g) and ethyl bromide (145 g). The reactor was sealed and the mixture heated to 97° C. Heating at 97° C. was continued for 18 hours. Distillation of excess ethyl bromide was controlled by the upper valve of the reactor followed by vacuum distillation. Finally, the solution was diluted with de-ionized water (DIW) (47 g). The weight of the aqueous concentrate was 250 g and the concentration of 2-MEPy was 79.3 weight % (argentometric titration); yield, 96%.

Example 2

Preparation of 2-MEPy Using a Slight Excess of Ethyl Bromide

A pressure reactor was equipped with a mechanical stirrer, a magnetic relay and a thermocouple well. The reactor was purged with nitrogen and then charged with 2-picoline (654 g), sealed and heated to 80-90° C. Ethyl bromide (774-850 g) was slowly added during 60-90 minutes, at 92-110° C. Heating at 100° C. was continued for 1 hour. Water was added and excess ethyl bromide was distilled-off as aqueous azeotrope under reduced pressure. Finally, the solution was diluted with DIW. The weight of the aqueous concentrate was 1722 g and the concentration of 2-MEPy 77.8 weight % (argentometric titration); yield, 95%.

Example 3

Preparation of 2-MEPy Using a Slight Excess of 2-Picoline

A pressure reactor was equipped with a mechanical stirrer, a magnetic relay and a thermocouple well. The reactor was purged with nitrogen and charged with 2-picoline (662 g). Vacuum was applied (0.15 bara), the reactor was sealed and heated to 95° C. following which the pressure increased to about 0.4 bara. Ethyl bromide (763 g) was then added during 120 minutes, at 95-100° C. Heating at 100° C. was continued for additional one hour (at the end of cooking period, the pressure was 0.4 bara). Vacuum and dry evaporation were applied for 1 hour, in order to remove the residual 2-picoline. Water was then added (300 mL) and second vacuum distillation was performed (50 mL were removed). The weight of the aqueous concentrate was 1605 g and the concentration of 2-MEPy 85 weight % (argentometric titration); yield, 97%.

Example 4 (Comparative)

Preparation of 2-MEPy According to the Procedure Described in Journal of the American Chemical Society, 21, p. 828-854 (1899)

A 500 mL round bottom flask was equipped with a magnetic stirrer, a condenser and a thermocouple well. The flask was charged with 2-picoline (116.5 g) and ethyl bromide (136.3 g) and gradually heated under reflux temperature. After 20 min. (47° C.) turbidity appeared. The mixture was further heated to 59° C. (reflux) and heated under reflux for four hours. The final mixture, consisting of a thick slurry, was cooled during which time the solids precipitated and a clear pinkish upper liquid layer formed. Analysis indicated that the conversion of 2-Picoline to 2-MEPy was about 20%.

Example 5

Preparation of 2-MEPy in Aqueous Medium

A pressure reactor was equipped with a mechanical stirrer with a magnetic relay and a thermocouple well. The reactor was purged with nitrogen and charged with 2-picoline (101.3 g) and de-ionized water (DIW) (20 mL), sealed and the mixture was heated to 92° C. Ethyl bromide (97.9 g) was slowly added during 3 hours, at 92-100° C. The mixture was heated at 94-100° C. for additional 2 hours, then cooled, and the pressure was released. The crude solution was diluted with DIW (24 mL) and excess 2-picoline was distilled-off as aqueous azeotrope, under reduced pressure. Finally, the residue was diluted with DIW. The weight of the aqueous concentrate was 251 g and the concentration of 2-MEPy was 66.1 weight % (argentometric titration); yield, 91.5%.

Example 6

Preparation of 3-MEPy in Aqueous Medium

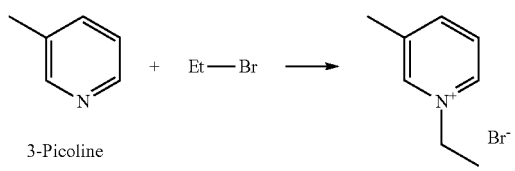

3-Picoline

A pressure reactor was equipped with a mechanical stirrer with a magnetic relay and a thermocouple well. The reactor was purged with nitrogen and charged with 3-picoline (101.3 g) and DIW (25 mL). The reactor was sealed and the mixture was heated to 96° C. Ethyl bromide (97.9 g) was slowly added during 2 hours, at 96-104° C. The mixture was heated at 100° C. for additional 3.5 hours, after which time the pressure was released. The crude solution was diluted with DIW and excess 3-picoline was distilled-off as aqueous azeotrope, under reduced pressure. Finally, the residue was diluted with DIW. The weight of the aqueous concentrate was 260 g and the concentration of 3-MEPy was 66.6 weight % (argentometric titration); yield, 95.6%.

Examples 7-11 (of the Invention) and 12 (Comparative)

HBr Electrolyte Solutions which Contain 2-MEPy, 3-MEPy or Mixtures Thereof as Additives To demonstrate the effect of 2-MEPy, 3-MEPy and mixtures thereof (at molar ratios of 1:3, 1:1 and 3:1), 12 ml samples were prepared, with electrolyte compositions corresponding to two distinct states of charge (SOC) of hydrogen/bromine cell. The states of charge are defined by different concentrations of hydrogen bromide and elemental bromine, which were present in the samples in suitable amounts in order to match the state of charge investigated:

State A (at the beginning of the charge process, i.e., SOC=0%): HBr concentration of 34 wt % and 0.2M of elemental bromine. State B (at the end of the charge process, i.e., SOC=100%): HBr concentration of 22 wt % and 0.2M of elemental bromine.

In each sample, the total concentration of the additive (either 2-MEPy, 3-MEPy or a mixture thereof) was 0.8M. The samples were stored at room temperature for 24 hours after preparation before any measurement was conducted. The samples were tested for the following properties: the temperature at which a solid phase is formed in the electrolyte, free bromine concentration, specific conductivity and vapor pressure using the following methods:

1) The specific conductivity of the hydrogen bromide acid solutions containing the additives was measured at room temperature, before the addition of bromine to the samples.

2) The temperature at which the formation of a solid phase takes place in the electrolyte solution was determined by gradually cooling the samples from RT (approximately 25-30° C.) to −15° C. The cooling regime was as follows: the temperature was decreased from RT down to 15° C. with a cooling rate of 0.2° C./min, and kept at 15° C. for 4 hours and so forth down to −15° C. At each of the following temperatures: 15° C., 10° C., 5° C., 0° C., −5° C., −10° C. and −15° C., the solution was maintained at a constant temperature for four hours. The cooling test was performed in polyethylene glycol solution, until the formation of crystals was observed.

3) The bromine concentration in the aqueous phase above the complex phase was determined by a conventional iodometric titration technique. Each vial was sampled three times at room temperature.

4) The vapor pressure above the electrolyte solutions containing the additives was measured at 20-26° C. according to "Vapor pressures of bromine-quaternary ammonium salt complexes for zinc-bromine battery applications" Satya N. Bajpal *J. Chem. Eng. Data* 26, 2-4 (1981).

For the purpose of comparison, the use of N-ethyl-4-methylpyridinium bromide (abbreviated 4-MEPy) as a potential additive in hydrogen/bromine cells was also investigated.

The results are tabulated in Table 1 below, in which the following abbreviations are used:

(i) The letters A or B next to the Example's number indicate the SOC that was investigated and hence the concentration of the electrolyte in terms of HBr and elemental bromine as set forth above;

(ii) the notation 2-MEPy/3-MEPy (x:y) indicates a mixture consisting of 2-MEPy and 3-MEPy in which the molar ratio between the two components is x to y.

TABLE 1

| Ex. | Additive | Temperature at which a solid phase was observed | [Br$_2$] in aqueous phase (%) | Specific conductivity (mS/cm) | Vapor pressure (mmHg) |
| --- | --- | --- | --- | --- | --- |
| 7A | 2-MEPy | 5° C. | 0.9 | 588 | 24 |
| 7B | 2-MEPy | −10° C. | 1.05 | 582 | 21 |
| 8A | 3-MEPy | −5° C. | 0.65 | 623 | 24 |
| 8B | 3-MEPy | −10° C. | 0.99 | 605 | 18 |
| 9A | 2-MEPy/3-MEPy (3:1) | −5° C. | 0.93 | 561 | 22 |

TABLE 1-continued

| Ex. | Additive | Temperature at which a solid phase was observed | [Br$_2$] in aqueous phase (%) | Specific conductivity (mS/cm) | Vapor pressure (mmHg) |
| --- | --- | --- | --- | --- | --- |
| 9B | 2-MEPy/3-MEPy (3:1) | −10° C. | 1.12 | 569 | 27 |
| 10A | 2-MEPy/3-MEPy (1:1) | −10° C. | 0.81 | 456 | 35 |
| 10B | 2-MEPy/3-MEPy (1:1) | −10° C. | 0.88 | 562 | 34 |
| 11A | 2-MEPy/3-MEPy (1:3) | −10° C. | 0.49 | 600 | 36 |
| 11B | 2-MEPy/3-MEPy (1:3) | −10° C. | 1.16 | 566 | 38 |
| 12A | 4-MEPy | 25° C. | N/A | 610 | N/A |
| 12B | 4-MEPy | 25° C. | N/A | 597 | N/A |

Example 13

Properties of Concentrated Aqueous Solutions of 2-MEPy, 3-MEPy and Mixtures Thereof Aqueous solutions of 2-MEPy, 3-MEPy and mixtures thereof at concentrations of 80% by weight were prepared and the viscosities and conductivities of the solutions were measured. The viscosity was measured using Brookfield viscometer. The results are set out in Table 2.

TABLE 2

| Solution Composition and concentration | Viscosity (cP) | Specific conductivity (mS/cm) |
| --- | --- | --- |
| Aqueous solution of 2-MEPy (80% by weight) | 60 ± 2 | 8 |
| Aqueous solution of 3-MEPy (80% by weight) | 18 ± 6 | 31 |
| Aqueous solution comprising a mixture of 2-MEPy and 3-MEPy at molar ratio of 3:1 (80% by weight) | 36 ± 15 | 14 |
| Aqueous solution comprising a mixture of 2-MEPy and 3-MEPy at molar ratio of 1:3 (80% by weight) | 25 ± 12 | 20 |

Examples 14 and 15

Preparation of 2-MEPy:3-MEPy Mixtures

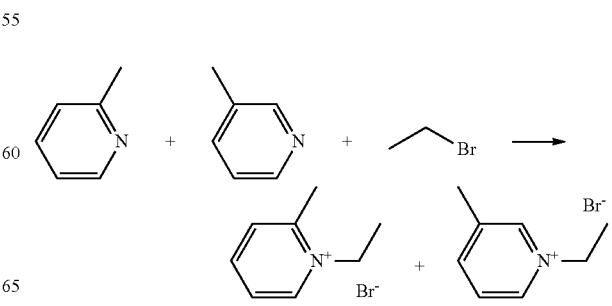

2-MEPy/3-MEPy Mixture (5:1 Ratio):

A double surface pressure reactor (1 L) was equipped with a magnetic stirrer relay, a condenser, a thermocouple well and a dosing pump. The reactor was purged with nitrogen and then charged with 2-picoline (465.8 g) and 3-Picoline (93.2 g). The reactor was heated to 90° C. and 1-bromoethane fed using a dosing pump during 2 hours (max. pressure 2.7 bara). The mixture was further heated at 100-110° C. for 1 hour. The pressure was released and vacuum was gradually applied for 30 minutes. DIW (400 mL) was added and vacuum distillation performed until 110 g distillate was collected. Final product, 1482 g, 80.9 weight % (argentometric titration); yield, 98.9%.

2-MEPy/3-MEPy Mixture (1:5):

A double surface pressure reactor (1 L) was equipped with a magnetic stirrer relay, a condenser, a thermocouple well and a dosing pump. The reactor was purged with nitrogen and then charged with 2-picoline (93.2 g) and 3-Picoline (465.8 g). The reactor was heated to 90° C. and 1-bromoethane fed using a dosing pump. After half of the ethyl bromide was fed the temperature was gradually raised to 120° C. (overall feed time, 2 hours; max. pressure, 3.9 bara). The mixture was further heated at 126° C. for 0.5 hour. The pressure was released and vacuum was gradually applied for 30 minutes. DIW (400 mL) was added and vacuum distillation performed until 112 g distillate was collected. Final product, 1473 g, 79.9 weight % (argentometric titration); yield, 97%.

The invention claimed is:

1. A process for preparing an aqueous solution of N-ethyl-2-methylpyridinium bromide (2-MEPy), comprising reacting 2-picoline and ethyl bromide in a pressure reactor at a temperature above the melting point of the reaction mixture, combining the reaction product with water, wherein said reaction product consists essentially of 2-MEPy in a liquid form, and recovering an aqueous solution of 2-MEPy, wherein the reaction is free of solvent, and said process does not involve the preparation or isolation of 2-MEPy in a solid form.

2. A process according to claim 1, wherein the reaction is carried out at a temperature above 90° C.

3. A process according to claim 2, comprising charging a pressure reactor with 2-picoline, sealing and heating the reactor, gradually feeding ethyl bromide in an excess of from 1 to 10 molar %, allowing the reaction to reach completion at a temperature above 95° C. to form a reaction product consisting essentially of 2-MEPy in a liquid form, and combining the liquid reaction product with water.

4. A process for preparing an aqueous solution of N-ethyl-2-methylpyridinium bromide (2-MEPy) or N-ethyl-3-methylpyridinium bromide (3-MEPy), comprising reacting in an aqueous medium ethyl bromide with 2-picoline or 3-picoline, respectively,
wherein the amount of water is not more than 20 weight % relative to the total weight of the reaction mixture.

* * * * *